(12) United States Patent
Ranne

(10) Patent No.: US 9,788,937 B1
(45) Date of Patent: Oct. 17, 2017

(54) CLIP AND A SYSTEM FOR LIGAMENT RECONSTRUCTION

(71) Applicant: CC-Clip Oy, Turku (FI)

(72) Inventor: Juha Ranne, Turku (FI)

(73) Assignee: CC-CLIP OY, Turku (FI)

( * ) Notice: Subject to any disclaimer, the term of this patent is extended or adjusted under 35 U.S.C. 154(b) by 0 days.

(21) Appl. No.: 15/264,917

(22) Filed: Sep. 14, 2016

(51) Int. Cl.
 *A61B 17/04* (2006.01)
 *A61F 2/08* (2006.01)

(52) U.S. Cl.
 CPC ..... *A61F 2/0811* (2013.01); *A61F 2002/0835* (2013.01); *A61F 2002/0864* (2013.01); *A61F 2002/0888* (2013.01); *A61F 2310/00017* (2013.01); *A61F 2310/00023* (2013.01)

(58) Field of Classification Search
 USPC ........... 623/13.11–13.14; 606/72, 74, 76, 96, 606/144, 286, 289, 300
 See application file for complete search history.

(56) References Cited

U.S. PATENT DOCUMENTS 8,323,338 B2 * 12/2012 LeBeau ............. A61B 17/0401 606/232

* cited by examiner

*Primary Examiner* — Yashita Sharma
(74) *Attorney, Agent, or Firm* — Ziegler IP Law Group, LLC

(57) ABSTRACT

The present invention relates to a clip system for ligament reconstruction, comprising a clip comprising portions forming a loop-like closed structure extending in two directions, suitable for being placed in a hole drilled in a bone, and a button-like counterpart.

18 Claims, 5 Drawing Sheets

CLIP AND A SYSTEM FOR LIGAMENT RECONSTRUCTION

FIELD OF THE INVENTION

The present invention relates to a clip and a system useful for ligament reconstruction. The system comprises a clip and a counterpart, which are intended to be placed on bones that need to be re-connected through a replacement ligament after ligament rupture.

BACKGROUND

Mammals have several joints where bones are attached to each other via ligaments. The ligaments may rupture in accidents or a person may be born with a faulty ligament. Typically, when a ligament has ruptured, it is not possible to reattach the end together, as the ligament tends to shrink very fast.

For example, an acromioclavicular joint (AC-joint) separation typically occurs after falling on the shoulder. In type III-V dislocations surgical intervention is often considered. An arthroscopic double bundle coracoclavicular (CC) ligament reconstruction technique using a semitendinosus tendon (ST) autograft has been introduced to treat AC dislocations. The tendinous reconstruction may be used both in acute and chronic cases.

The key element in this technique is the positioning of the hamstring tendon graft. The anterior limb of the graft projects superiorly and replaces the trapezoid ligament. The dorsal limb of the graft is wrapped around the dorsal edge of the clavicle reconstructing the conoid ligament. As the ST graft shares the same drill holes with the temporary fixation apparatus, there is only one 6-mm drill hole in the clavicle and a 4.5-mm drill hole in the neck of the coracoid. This effectively stabilizes the AC-joint and prevents anterior-posterior translation. For additional fixation, titanium buttons connected with double number five Fiberwire® or Fibertape® have been utilized.

For this arthroscopic coracoclavicular ligament reconstruction, there exists several different clip systems, for example known under the tradenames GraftWasher®, Arthro W-D, TightRope® or GraftRope®. However, all the existing clip systems have some disadvantages. For example, the clip system sold under the tradename Graft-Washer® has some disadvantages for both the surgeon and the patient. Indeed, with this clip system, two rather large FiberWire® or FiberTape® knots remain on top of the washer on the clavicle. These knots may cause infections and sometimes they even need to be removed after a few years as they case irritation underneath the skin. Furthermore, the holes of the GraftWasher® for the wires are somewhat apart from each other: 8 and 10 mm. This distance results in the four wire limbs to form a funnel-shape bunch of heavy wires in the 6 mm clavicular drill hole. In the long run this may lead to tunnel widening up to 10 mm of the drill hole. This has indeed been detected in follow up X-rays. Moreover, for some patients, the rim of the GraftWasher® is too wide. The graft limbs cross over the dorsal rim of the washer and at 4 mm it may be unnecessary wide, resulting in the graft not being able to attach to the bone. A yet further disadvantage is that an interference screw is needed when using the GraftWasher®, thus adding more foreign material to the body.

Indeed, it would be advantageous if the interference screw could be avoided, as it adds foreign material to the body, possibly resulting in problems of irritation and/or infection.

Moreover, in the case of coracoclavicular ligament reconstruction, the fixation is located almost immediately underneath the skin and on the bone. It is thus very prone to infection, while it may also lead to functional defects as well as be cosmetically unaesthetic.

Furthermore, the buttons used underneath the coracoid sometimes seem to grind the wires broken due to movement and friction against the sub-coracoid button.

OBJECTS AND SUMMARY OF THE INVENTION

It is an object of the present invention to provide an improved clip system for ligament reconstruction, that does not present the disadvantages of the prior art. For example, the present clip system is designed to need only one small knot in the clavicle, thus avoiding the rather large knot construction described above. A further aim is to eliminate the need for an interference screw. A yet further aim is to avoid problems with the connecting wires, i.e. to avoid the funnel form described above in connection with one particular prior art clip system. In general, the aim is to provide a clip system that is safer and easier to place by the surgeon, and to provide a clip system that minimises the risks for the patient after the operation, be it infection or failure of the clip system in general.

The present invention relates to a clip for ligament reconstruction, comprising at least eight portions, wherein
 each portion has independently a cross-section having a form of a rectangle or an ellipse, wherein the largest dimension of the cross-section is from 0.5 to 3 mm,
 each portion has a first end and a second end, a distance between the first end and the second end defining a length of the portion, and the portions being
  a first portion defining a first plane, its length being from 4 to 10 mm,
  a second portion attached by its first end to the second end of the first portion, essentially perpendicular to the first portion, in the first plane, its length being from 6 to 14 mm,
  a third portion attached by its first end to the second end of the second portion, essentially perpendicular to the second portion and parallel to the first portion, in the first plane, extending from the second portion in a direction parallel to the direction from the second end of the first portion towards the first end of the first portion, its length being from 10 to 24 mm,
  a fourth portion attached by its first end to the second end of the third portion, essentially perpendicular to the third portion and parallel to the second portion, in the first plane, extending from the third portion in a direction parallel to the direction from the second end of the second portion towards the first end of the second portion, its length being essentially identical to the length of the second portion,
  a fifth portion attached by its first end to the second end of the fourth portion, essentially perpendicular to the fourth portion and aligned with the first portion, in the first plane, extending from the fourth portion towards the first portion, its length being from 4 to 10 mm,
  a sixth portion attached by its first end to the second end of the fifth portion, essentially perpendicular to the fifth portion, in a second plane that is perpendicular to the first plane, its length being from 4 to 8 mm,
  a seventh portion attached by its first end to the second end of the sixth portion, essentially perpendicular to the sixth portion and parallel to the first portion, in the second plane, extending from the sixth portion in a direction parallel to the direction from the first end of the first portion towards the second end of the first portion, its length being from 2 to 7 mm, and an eight portion attached by its first end to the second end of the seventh portion and by its second end to the first end of the first portion, essentially perpendicular to the seventh portion and the first portion and parallel to the sixth portion, in the second plane, its length being essentially identical to the length of the sixth portion.

The present invention further relates to a system for ligament reconstruction, comprising a clip as described above and a counterpart, wherein the counterpart has essentially a shape of a rectangle or ellipse, wherein a largest dimension is from 8 to 14 mm and a smallest dimension is from 6 to 12 mm, and comprises at least two openings, wherein a largest dimension of each opening is from 1 to 6 mm and a smallest dimension of each opening is from 1 to 5 mm.

DETAILED DESCRIPTION OF THE INVENTION

Figure 1:
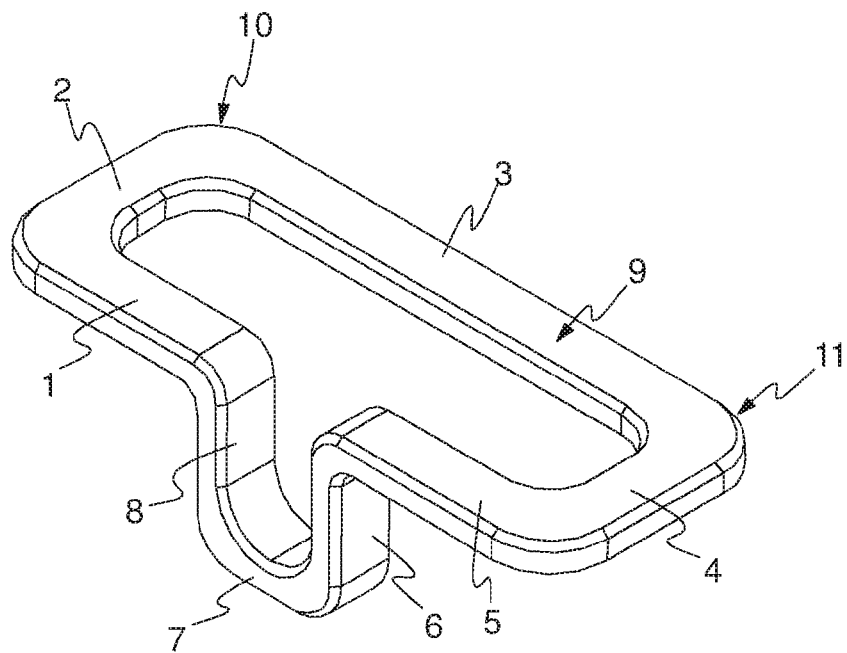
FIG. 1 schematically illustrates a clip according to a first embodiment.

The present invention relates to a clip for ligament reconstruction as described above and a system for ligament reconstruction, comprising a clip and a counterpart as described above. The present invention thus relates to a clip and a system for ligament reconstruction, comprising a clip comprising portions forming a loop-like closed structure extending in two directions, suitable for being placed in a hole drilled in a bone, and a button-like counterpart. These two parts are attachable to each other using connecting wires. The wires can be made using any biocompatible wire, cord, rope or tape that has sufficient strength. Some options are the products sold under tradenames FiberWire® or FiberTape®, for example in size 5. In the following, the term wire is used to designate all of these possible materials. Likewise, the term attachment point is used to designate the location where two portions are attached to each other. In the following, the clip system is mostly described, but it is obvious that the advantages listed for each part of the system, the clip or the counterpart, apply to also that particular part, even if used in connection with other parts. The advantages explained below thus apply mutatis mutandis to the clip and the counterpart, as the case may be.

The present clip system has several advantages. Indeed, by its structure, it eliminates the need for a large double knot on the bone, such as the clavicle when used for coracoclavicular ligament reconstruction. The present system also eliminates the need for an interference screw, as the clip loop and the knot in the drill hole sufficiently fix the graft against the drill hole wall. A yet further advantage is that the present clip system eliminates the funnel form of the connecting wires. Indeed, in this technique, the wires go straight from the counterpart to the clip. This fact also makes the connecting fixation maximally strong, as direction of the pull is straight. Moreover, the form of the counterpart, with two openings, allows the wire to be attached using a loop (preferably a larks head knot), which reduces friction to the wire, thus preventing wire failure due to breaking of the wire. Naturally, other types of attachment are also possible if required.

It is also believed that the third portion of the clip would not tilt when assembled, i.e. during operation and after it, because the direction of the wire pull is axial to the clip loop and tightly pulls it against the bone. Furthermore, the clip loop is aimed at being a tight fit in the drill hole with the graft limbs.

The present clip system is typically used with a ligament graft, and once the clip system is positioned in place during surgery, the dorsal limb of the graft presses the third portion of the clip against the bone.

As can be seen from the wording above, the portions of the clip form a closed structure having an opening in the middle, i.e. a kind of closed loop. This form also has advantages against a straight bar (without any opening). Indeed, using the loop shape, it is easy to handle the clip despite its small size, and once the wire is put through the loop, there is no danger of dropping the clip perioperatively. Thus the handling of the clip by the surgeon is easier and more secure.

In coracoclavicular ligament reconstruction, the dorsal graft limb comes around the posterior edge of the clavicle. There may thus be a danger that the pressure of the graft induces resorption of the clavicular cortex, and there is even clinical evidence showing it happening. When the present clip is used, the graft limb has to go over the third portion of the clip, therefore reducing the pressure on the bone. When the third portion is at least 2 mm wide, the effect is even improved. Thus the present clip allows to obtain this same benefit as is obtained with the above-discussed Graft Washer®, while using a narrower and lighter option with other advantages.

The dimensions of the clip are listed above. These dimensions are mainly based on the dimensions of the bones in connection of which the present clip system is intended to be used. The clip has a longitudinal or elongated shape, i.e. the length of the third portion is the largest one. The elongated shape distributes the pressure on the bone preventing the clip from sinking into the bone.

For example, for use in coracoclavicular ligament reconstruction, the clip can be manufactured in different sizes, where only the largest dimension of the clip, i.e. the length of the third portion, changes. This possibility is due to the fact that although the anterior-posterior surface of the clavicular bone is convex and the convexity varies among patients, there is longitudinally not that much curvature and an elongated shape of the clip fits well on the bone. Similar considerations apply to other ligament reconstructions. It is also possible to manufacture the clip in a material (such as fibre-reinforced composite material) that is tough yet flexible. Such material can change its form slightly to conform to the shape of the bone to which it is attached.

As has been mentioned above, an object of the present disclosure is to provide a clip system that does not require the use of an interference screw. This object is achieved with the present clip system, when a clip having the above-listed dimension is used together with a drill hole of 6 mm in diameter. Indeed, in this case the ligament graft passes the hole twice. The outer dimensions of the side loop formed of the sixth, seventh and eight portion are for example 5 mm (length) and 2 mm (width). The side loop is inserted into the drill hole, where it squeezes the ligament grafts against the drill hole wall. The wire used for inserting the various parts of the system and for holding them in place while the ligament grafts attach to the bone is attached by using one to three knots. These knots can at least partly enter the drill hole, too, thus making this space even tighter. Thus no interference screw is required.

As explained above, the first to fifth portion form an essentially rectangular shape. By essentially rectangular, it is meant that the corned can be rounded off. For example, according to an embodiment, the first portion, the second portion, the third portion, the fourth portion and the fifth portion form a stadium like form factor, wherein an inner radius in a corner defined by an attachment point between the portions is from 1 to 3 mm and an outer radius of the corners is from 2 to 6 mm.

The same applies to the side loop formed by the sixth, seventh and eighth portion. Indeed, according to another embodiment, the sixth portion, the seventh portion and the eight portion form a half stadium like form factor, wherein an inner radius in a corner defined by an attachment point between the portions is from 1 to 3 mm and an outer radius of the corners is from 2 to 6 mm.

According to another embodiment, the portions have an essentially rectangular cross section. In this case, each portion has a first side surface and a second side surface that are essentially parallel to each other, a distance between the first side surface and the second side surface defining a width of the portion, the width being from 1 to 3 mm. Furthermore, each portion has a top surface and a bottom surface that are essentially parallel to each other, a distance between the top surface and the bottom surface defining a thickness of the portion, the thickness being from 0.5 to 2 mm. In this embodiment, the top surface of each of the first to fifth portion is parallel to the first plane in which the portion is, or the top surfaces can be considered to define the first plane.

According to another embodiment, the portions can also have cross sections that are slightly rounded or circular. For example, the surface that is to be arranged in contact with the bone, such as the surface of the first to fifth portion, is preferably completely or mostly flat. The surface that will be towards the skin of the patient can be slightly rounded or flat. Indeed, preferably all surfaces that enter into contact with the bone are flat, in order to increase the contact surface with the bone to enhance attachment of the clip and/or the counterpart to the bone. These surfaces can also be slightly roughened, i.e. not completely smooth, again to increase contact surface.

According to another embodiment, the shape of the seventh portion can be slightly curved, in order to better adjust to the contact with the graft. Likewise, all surfaces that come into contact with the ligament graft can be slightly rounded.

Sharp edges should preferably be avoided on all portions of the clip and of the counterpart.

According to yet another embodiment, each portion has essentially the shape of a rectangle, wherein the first end and the second end are the ends furthest away from each other. The distance between the first end and the second then defines the length of the portion.

According to an embodiment, the clip and the counterpart are independently made of a material selected from a group consisting of medical grade titanium, medical grade steel, polyether ether ketone and biocompatible fibre-reinforced polymeric composites. One preferred material is medical grade titanium, due to its weight compared to its strength. All the materials used need naturally be biocompatible and accepted for use in implanted devices. Fibre-reinforced polymeric composites may contain any suitable components known per se, such as glass fibres and poly(methyl methacrylate).

The present system can be used together with an autologous graft, i.e. a ligament harvested from the patient, or it can be used with an artificial ligament craft.

The counterpart used in connection with the clip can have various forms. It may have a form of a rectangle (including a square) or of an ellipse (including a circle). The counterpart has two openings, making it look like a button. The two openings are separated by a cross bar. Preferably all the edges are rounded, in order to prevent friction causing the wire to break. The size of the counterpart, including the size of the openings and the cross bar, are ideally such that they are just wide enough for the wire but not too wide such that it does not allow movement of the wire loop. As significant movement is not allowed, friction to the wire is reduced friction. The openings can be made larger for the cases when a double wire is desired, for example for patients with heavier build, thus requiring higher forces. Again, the openings and the cross bar should be just wide enough to house a double wire loop and to prevent it from moving. The openings should ideally however not be too small, but to allow the rope to slide therein, to make the assembly process easy.

According to an embodiment, the counterpart has the shape of a rectangle, its largest dimension is from 9 to 11 mm and its smallest dimension is from 8 to 10 mm. As a particularly advantageous option, the counterpart has the shape of a square, and its dimension (i.e. side length) is from 9 to 11 mm. When the counterpart has a rectangular shape, the shape of the openings is preferably essentially a rectangle, its largest dimension is from 5 to 7 mm and its smallest dimension is from 1 to 3 mm.

According to another embodiment, the counterpart has the shape of a circle, and its diameter is from 9 to 11 mm. Indeed, circle is a shape comprised in ellipses. In this case, the shape of the openings is preferably essentially a segment of a circle, its largest dimension is from 4 to 6 mm and its smallest dimension is from 1 to 3 mm.

The openings in the counterpart thus extend through the whole thickness of the counterpart. The dimensions of the counterpart can be for example for a rectangular form (or rather, a square form), side length 10 mm, length of each opening 6 mm and width of each opening 2 mm, with a width of the cross bar 2 mm. The opening can thus have an essentially rectangular form, too. The thickness of the counterpart can be for example 1 mm. The dimensions of the counterpart having an elliptical form (or rather, a circular form), diameter 10 mm, width of the cross bar 2 mm and thickness of the counterpart 1 mm. In this embodiment, the shape of the openings can be semi-circular, with a radius of 2 mm, or a segment of a circle.

The dimensions of the various portions of the clip are given above. Some preferred dimensions are as follows, each being selectable independently from each other as long as all the portions form a complete loop. Indeed, preferably, the length of the first portion is from 4.5 to 7.5 mm, the length of the second portion and of the fourth portion is from 7 to 10 mm, the length of the third portion is 14 from to 20 mm, the length of the fifth portion is from 4.5 to 7.5 mm, the length of the sixth portion and of the eight portion is from 4 to 7 mm, and/or the length of the seventh portion is from 4 to 6 mm. According to another preferred embodiment, the length of the fifth portion is identical to the length of the first portion.

For use in coracoclavicular ligament reconstruction, the clip can for example be manufactured in three sizes, where the length of the third portion is either 14 mm, 16 mm or 20 mm. Indeed, the smaller clips are suitable for lighter and smaller patients and the largest for heavily built patients. Typically, the length of the seventh portion is the same in all sizes of the clip, for example 5 mm, as well as the length of the second and fourth portions, for example 8 mm. The length of the first and fifth portions thus varies according to the length of the third portion, and their lengths are typically identical (i.e. length of the third portion minus length of the seventh portion divided by two). The side loop formed by the sixth, seventh and eight portion is typically located in the middle of the side of the clip. Most typically, the lengths of the sixth and eights portions are also identical, for example 6 mm.

Typically, the diameter of the drill hole is 6 mm. In this case, the outer diameter of the part of the clip formed of the sixth, seventh and eight portions, i.e. the length of the seventh portion is preferably 5 mm. With the two parts of ligament grafts going through the drill hole, a tight fit is achieved.

In the following, the surgical technique for an arthroscopic double bundle coracoclavicular ligament reconstruction using a semitendinosus allograft is explained in detail. Indeed, the present clip system is especially suitable for this type of ligament reconstruction, although it is useful also for other ligament reconstructions, such as in some ankle operations.

A semitendinosus tendon graft is harvested from the ipsilateral leg of the patient. The graft thickness is measured, while the optimal thickness of the graft is 4 mm. Alternatively, a 0.5×16 cm Artelon® artificial tendon graft may be used. A number 2 passing wire is fixed in one end of the graft using a whip stitch wire. A combination of the clip, the counterpart and number 5 braided wire are used to support the reconstruction and the tendon graft. A number 2 passing wire is added to the end of the number 5 tape loop.

Four portals are used for the arthroscopy: posterior (P), lateral (L), anterolateral (AL) and anterior (A). A 2 cm clavicular incision is made on the dorsal edge of the clavicle to expose the bone for subsequent drilling. In chronic cases an additional incision may be needed over the AC-joint to release the attachments around the distal clavicle. It is important to mobilize the distal clavicle well so as to achieve proper repositioning.

The operation is initiated by inserting the arthroscope into the joint through the posterior portal. The lateral portal is marked with a needle in front of the long head of the biceps tendon, allowing proper angle to the neck of the coracoid. The needle may be left in place. The arthroscope is then moved to the subacromial space viewing through the P portal. The coraco-acromial ligament is located with the help of the existing needle. The arthroscope is then moved to the L-portal. The primary camera position during the actual reconstruction is in the L portal. The AL and A portals are established with the help of a needle. It is important to have an easy access to the neck of the coracoid through both portals. The location of the clavicular incision is marked with a needle behind the dorsal clavicle. It is also important to have an easy access from the dorsal clavicle to the coracoid neck area.

Debridement and sufficient exposure is done around the coracoid process and the clavicle. First a 4-4.5 mm diameter hole, depending on the thickness of the graft, is drilled through the clavicle and the coracoid process using conventional drill guides for this purpose. The clavicular drill hole is then enlarged to a diameter of 6 mm. The cortex of the dorsal edge of the clavicle is roughened with a rasp to enhance the attachment of the dorsal graft limb. The passing wires for both the graft and the fixation apparatus are pulled through the holes drilled in the bone using the lasso technique. A straight lasso device may be used for this purpose. The lasso loop should be used "upside down" to avoid division of the distal lasso.

The graft should be inserted first, by first pulling the passing wire running to the AL portal through the clavicular and coracoid drill holes. Then the passing wire is pulled through the C portal behind the clavicle. Then a loop of the passing wire is pulled back again to the AL portal, leaving the free end of the passing wire sticking out behind the clavicle. The graft is then pulled to the AL portal by the proximal part of the passing wire loop. Finally the graft end is pulled out behind the clavicle by the free end of the passing wire. This procedure makes it easier to pass the graft.

The present clip system is then inserted. The number 5 wire loop is passed through the drill holes beside the graft and out of the AL portal. The counterpart is attached to the loop and pulled in by the number 5 wire ends. It sets to its place under the coracoid and one end of the passing wire is slipped through the clip. The end of the anterior limb is slipped straight through the clip. The end of the dorsal limb is taken over the third portion of the clip, slipped into the clavicular drill hole behind the anterior limb and then drawn to the AL portal using the lasso technique. Therefore, the dorsal limb comes most dorsally through the calvicular drill hole. The anterior graft limb is in the middle. Most anteriorly comes the clip loop with the number 5 wire knot which squeezes both graft limbs against the dorsal drill hole wall.

At this point, with the entire length of the graft and the fixation apparatus in place, repositioning of the AC-joint is checked. It is important that the repositioning happens easily and without tension. If necessary, an incision may be done over the AC-joint to release scar attachments around the distal clavicle. In complicated chronic cases the distal clavicle resection may also be conducted at this point.

With the repositioning reliably completed, the clip system is tightened, tensioning the graft at the same time. The posterior limb is tensioned by pulling horizontally from the AL portal. The anterior limb is tensioned by pulling directly upwards. While keeping up the tension of the graft, the number 5 wire ends are tied. Finally the anterior graft end is wired on to the dorsal graft limb behind the clavicle. The excess of the graft ends are removed. The arthroscopic portals are closed with interrupted wires while the clavicular wound is closed in layers.

Even though the present description describes the coracoclavicular ligament reconstruction in detail, the present clip system can be used for other ligament reconstructions, such as for ankle syndesmosis rupture repair.

In the above description, the outer shape of the combined portions in the first plane is essentially rectangular. By essentially rectangular, it is meat a rectangular shape with rounded edges. Indeed, all edges of both the clip and the counterpart are rounded, in order to prevent irritation on tissue or bone or breaking the graft or the wire.

However, the overall shape of the combined portions in the first plane could also be elliptical. In this case, the first to fifth portions would still be placed end to end, but they would not be perpendicular to each other. The length each part would also be the distance between the part's first end and second end, but along the portion, i.e. along its curvature.

DETAILED DESCRIPTION OF THE DRAWINGS

FIG. 1 schematically illustrates a clip according to a first embodiment. The Figure shows the eight portions of the clip, namely first portion 1, second portion 2, third portion 3, fourth portion 4, fifth portion 5, sixth portion 6, seventh portion 7 and eight portion 8. As can be seen, all the attachments between the portions are at at least approximately right angles, i.e. the portions are perpendicular and form a loop-like form. In this embodiment, the top surfaces of the first to fifth portions (illustrated with the reference number 9 for the third portion) are in the first plane. The sixth to eight portions are then in a second plane that is perpendicular to the first plane.

As can be seen, the fifth, sixth, seventh, eighth and first portions can also be considered to be in a common plane, i.e. aligned. Their alignment is parallel to the longest direction of the third portion 3.

For illustration purposes, the first end 10 of the third portion 3 and its second end 11 are denoted. The first end 10 of the third portion 3 coincides with the second end of the second portion 2 and the second end 11 of the third portion 3 coincides with the first end of the fourth portion 4.

Figure 2:
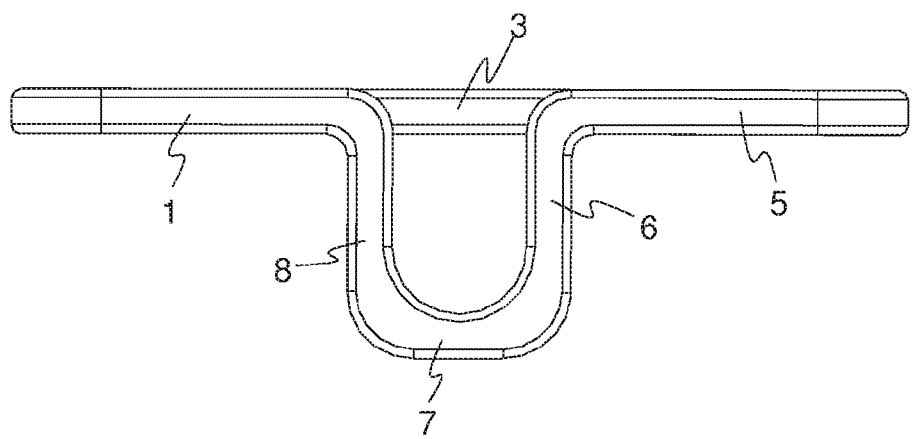
FIG. 2 schematically illustrates a clip according to the first embodiment, as a side view.

FIG. 2 schematically illustrates a clip according to the first embodiment, as a side view. In this view, it can be seen that the side loop formed by the sixth, seventh and eighth portions is arranged essentially in the middle of the side, i.e. the lengths of the first and fifth portions are essentially identical. This is believed to be a preferred embodiment, but naturally the side loop can be arranged elsewhere than in the middle, i.e. the lengths of the first and fifth portions can differ from one another.

Figure 3:
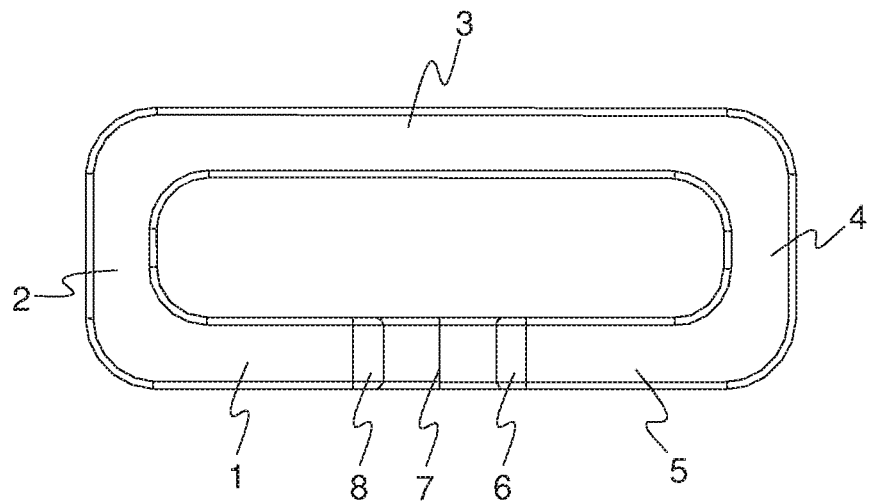
FIG. 3 schematically illustrates a clip according to the first embodiment, as a top view.

FIG. 3 schematically illustrates a clip according to the first embodiment, as a top view. In this embodiment, it can clearly be seen that preferably the edges are rounded and the overall forms a stadium like form factor, where the inner radiuses of the corners are smaller than the outer radiuses of the corners.

Figure 4:
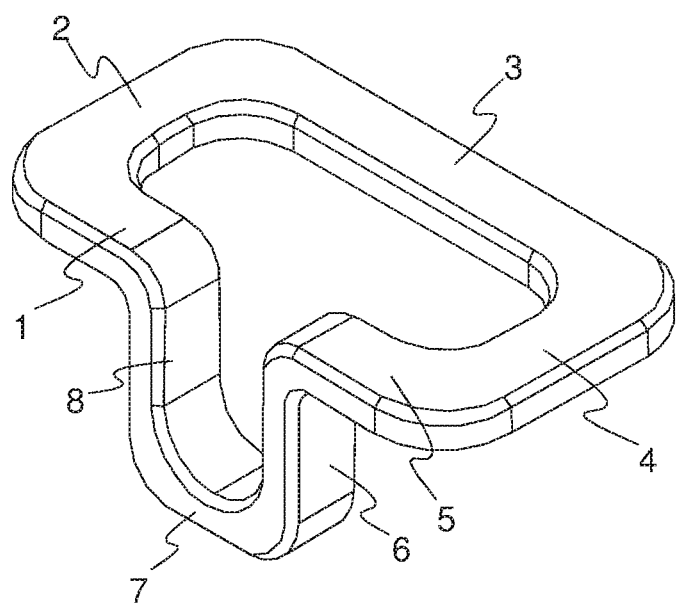
FIG. 4 schematically illustrates a clip according to a second embodiment.

FIG. 4 schematically illustrates a clip according to a second embodiment. This second embodiment differs from the first embodiment shown in FIGS. 1 to 3 only with respect to its dimensions. Indeed, the lengths of the second portion 2, fourth portion 4, sixth portion 6 and eight portion 8 are essentially identical to the lengths of the respective portions in the first embodiment, but the lengths of the first portion 1, third portion 3, fifth portion 5 and seventh portion 7 are smaller than the lengths of the respective portions in the first embodiment.

Figure 5:
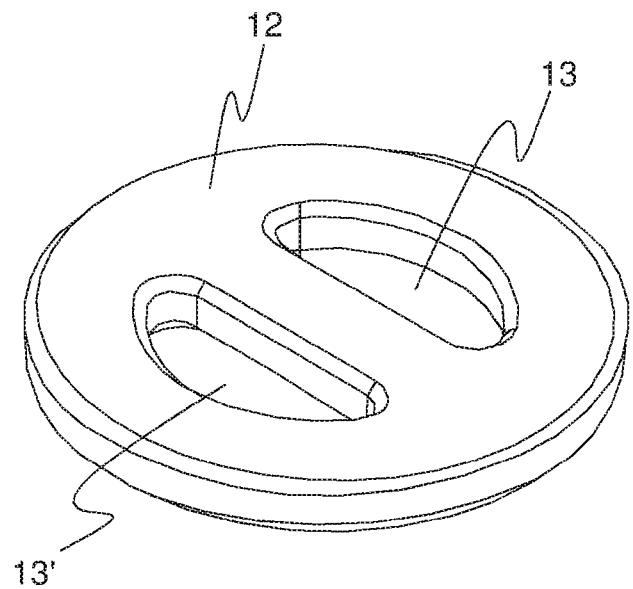
FIG. 5 schematically illustrates a counterpart according to a third embodiment.

FIG. 5 schematically illustrates a counterpart according to a third embodiment. The general shape of the counterpart 12 is circular, i.e. the counterpart has the form of a disc, where the thickness is significantly smaller than the radius. The counterpart 12 is equipped with two openings 13 and 13' that have the form of a segment of a circle.

Figure 6:
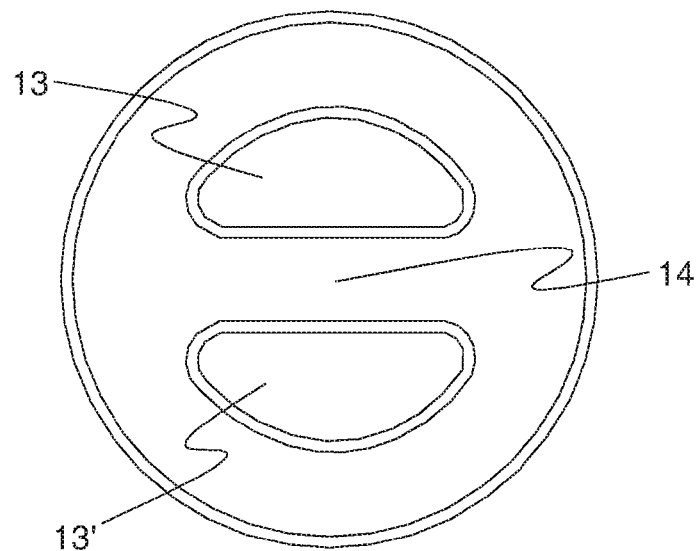
FIG. 6 schematically illustrates a counterpart according to the third embodiment, as a top view.

FIG. 6 schematically illustrates a counterpart according to the third embodiment, as a top view. In this Figure, it can be seen that the openings 13 and 13' have essentially the same shape and are mirror images one from another. The cross bar 14 separates the two openings 13 and 13' from each other.

Figure 7:
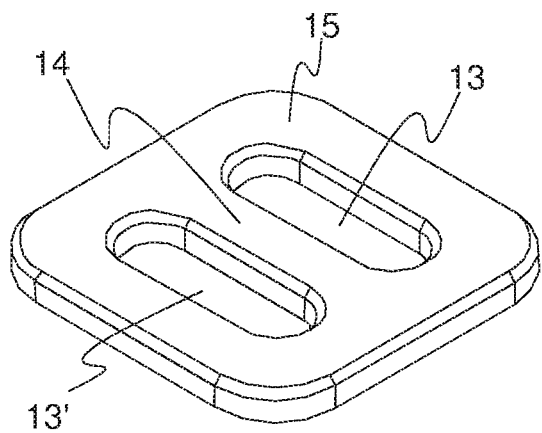
FIG. 7 schematically illustrates a counterpart according to a fourth embodiment.

FIG. 7 schematically illustrates a counterpart according to a fourth embodiment. The counterpart 15 in this embodiment has essentially the form of a square, with rounded edges. The two openings 13 and 13', separate by a cross bar 14, have the form of rounded rectangles, or stadium-form.

Figure 8:
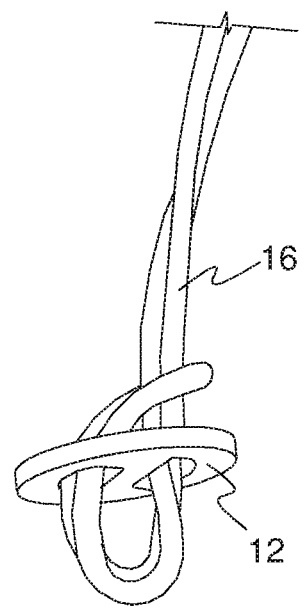
FIG. 8 schematically illustrates an embodiment of attachment of a counterpart to a wire.

FIG. 8 schematically illustrates an embodiment of attachment of a counterpart to a wire. The counterpart 12 (a round one in this Figure) is attached to the wire 16 by a loop, i.e. a larks head knot. This knot permits to avoid large knots that could both irritate the bone or the surrounding tissue and contribute to a funnel form of the wire. Indeed, the wire 16 is directed almost perpendicularly to the counterpart 12, and the two parts of the wire 16 are parallel to each other.

Figure 9:
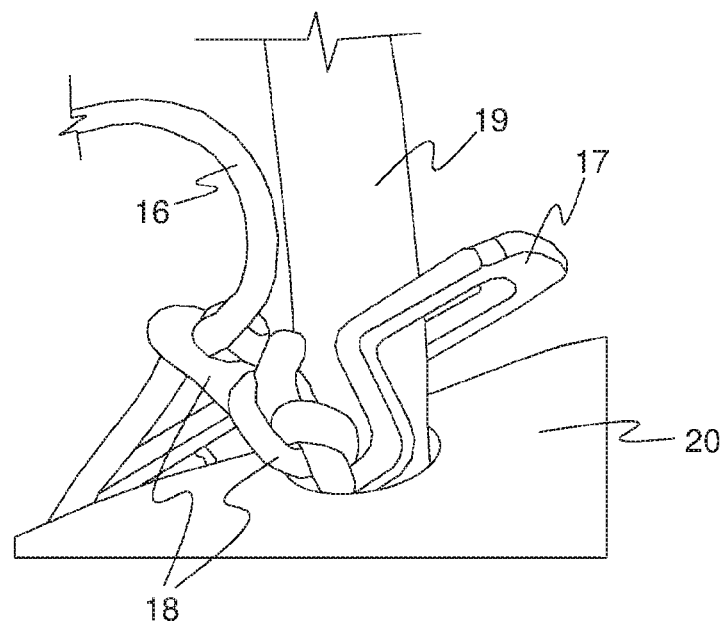
FIG. 9 schematically illustrates a clip according to an embodiment during the process of attachment of the clip system.

FIG. 9 schematically illustrates a clip according to an embodiment during the process of attachment of the clip system. The clip 17 has already been partially placed in a hole drilled in the bone 20, and attached with two knots 18 in the wire 16. The graft 19 passes through the clip 17, in the opening form by its loop-like structure.

Figure 10:
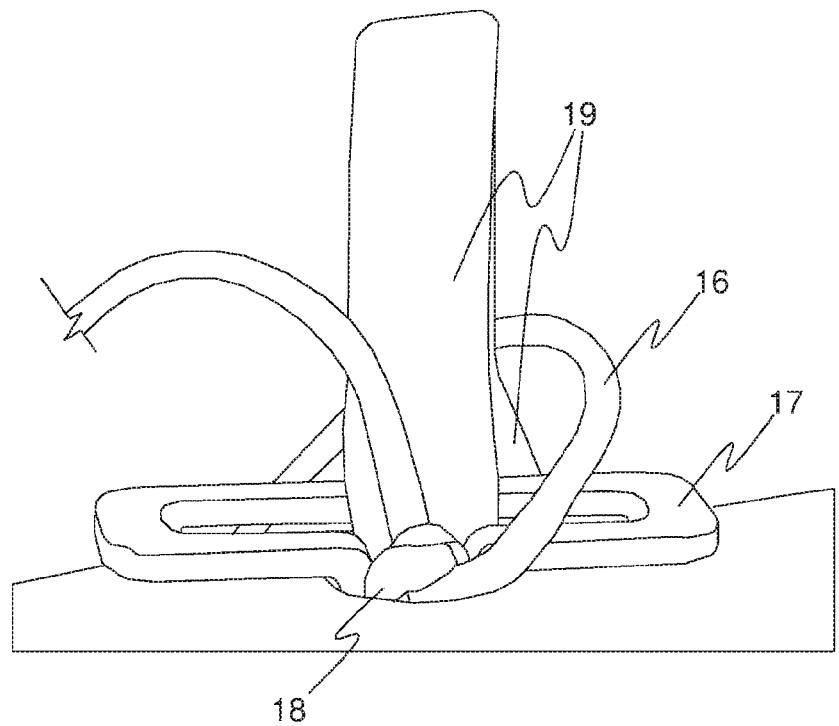
FIG. 10 schematically illustrates a further step of the process illustrated in FIG. 9.

FIG. 10 schematically illustrates a further step of the process illustrated in FIG. 9, where the side loop of the clip 17 is entirely in the hole drilled in the bone 20. As can be seen, only a part of the outermost knot 18 is visible, i.e. the remaining knots (two or three) are located inside the drilled hole, thus contributing to the tightening of the whole system. The graft 19 can be seen to pass both inside the clip 17 and behind it.

The invention claimed is:

1. A clip for ligament reconstruction, comprising at least eight portions, wherein
    each portion has independently a cross-section having a form of a rectangle or an ellipse, wherein the largest dimension of the cross-section is from 0.5 to 3 mm,
    each portion has a first end and a second end, a distance between the first end and the second end defining a length of the portion, and
    the portions being
        a first portion defining a first plane, its length being from 4 to 10 mm,
        a second portion attached by its first end to the second end of the first portion, essentially perpendicular to the first portion, in the first plane, its length being from 6 to 14 mm,
        a third portion attached by its first end to the second end of the second portion, essentially perpendicular to the second portion and parallel to the first portion, in the first plane, extending from the second portion in a direction parallel to the direction from the second end of the first portion towards the first end of the first portion, its length being from 10 to 24 mm,
        a fourth portion attached by its first end to the second end of the third portion, essentially perpendicular to the third portion and parallel to the second portion, in the first plane, extending from the third portion in a direction parallel to the direction from the second end of the second portion towards the first end of the second portion, its length being essentially identical to the length of the second portion, a fifth portion attached by its first end to the second end of the fourth portion, essentially perpendicular to the fourth portion and aligned with the first portion, in the first plane, extending from the fourth portion towards the first portion, its length being from 4 to 10 mm, a sixth portion attached by its first end to the second end of the fifth portion, essentially perpendicular to the fifth portion, in a second plane that is perpendicular to the first plane, its length being from 4 to 8 mm, a seventh portion attached by its first end to the second end of the sixth portion, essentially perpendicular to the sixth portion and parallel to the first portion, in the second plane, extending from the sixth portion in a direction parallel to the direction from the first end of the first portion towards the second end of the first portion, its length being from 2 to 7 mm, and an eighth portion attached by its first end to the second end of the seventh portion and by its second end to the first end of the first portion, essentially perpendicular to the seventh portion and the first portion and parallel to the sixth portion, in the second plane, its length being essentially identical to the length of the sixth portion;

wherein the first portion, the second portion, the third portion, the fourth portion and the fifth portion form a stadium like form factor, wherein an inner radius in a corner defined by an attachment point between the portions is from 1 to 3 mm and an outer radius of the corners is from 2 to 6 mm.

2. A clip according to claim 1, wherein the sixth portion, the seventh portion and the eight portion form a half stadium like form factor, wherein an inner radius in a corner defined by an attachment point between the portions is from 1 to 3 mm and an outer radius of the corners is from 2 to 6 mm.

3. A clip according to claim 1, wherein
each portion has a first side surface and a second side surface that are essentially parallel to each other, a distance between the first side surface and the second side surface defining a width of the portion, the width being from 1 to 3 mm, each portion has a top surface and a bottom surface that are essentially parallel to each other, a distance between the top surface and the bottom surface defining a thickness of the portion, the thickness being from 0.5 to 2 mm.

4. A clip according to claim 1, wherein each portion has essentially the shape of a rectangle, wherein the first end and the second end are the ends furthest away from each other.

5. A clip according to claim 1, wherein the clip is made of a material selected from a group consisting of medical grade titanium, medical grade steel, polyether ether ketone and biocompatible fibre-reinforced polymeric composites.

6. A clip according to claim 1, wherein the length of the first portion is from 4.5 to 7.5 mm.

7. A clip according to claim 1, wherein the length of the second portion and of the fourth portion is from 7 to 10 mm.

8. A clip according to claim 1, wherein the length of the third portion is 14 from to 20 mm.

9. A clip according to claim 1, wherein the length of the fifth portion is from 4.5 to 7.5 mm, preferably identical to the length of the first portion.

10. A clip according to claim 1, wherein the length of the sixth portion and of the eight portion is from 4 to 7 mm.

11. A clip according to claim 1, wherein the length of the seventh portion is from 4 to 6 mm.

12. A system for ligament reconstruction, comprising a clip and a counterpart, wherein the clip comprises at least eight portions, wherein each portion has independently a cross-section having a form of a rectangle or an ellipse, wherein the largest dimension of the cross-section is from 0.5 to 3 mm, each portion has a first end and a second end, a distance between the first end and the second end defining a length of the portion, and the portions being a first portion defining a first plane, its length being from 4 to 10 mm, a second portion attached by its first end to the second end of the first portion, essentially perpendicular to the first portion, in the first plane, its length being from 6 to 14 mm, a third portion attached by its first end to the second end of the second portion, essentially perpendicular to the second portion and parallel to the first portion, in the first plane, extending from the second portion in a direction parallel to the direction from the second end of the first portion towards the first end of the first portion, its length being from 10 to 24 mm, a fourth portion attached by its first end to the second end of the third portion, essentially perpendicular to the third portion and parallel to the second portion, in the first plane, extending from the third portion in a direction parallel to the direction from the second end of the second portion towards the first end of the second portion, its length being essentially identical to the length of the second portion, a fifth portion attached by its first end to the second end of the fourth portion, essentially perpendicular to the fourth portion and aligned with the first portion, in the first plane, extending from the fourth portion towards the first portion, its length being from 4 to 10 mm, a sixth portion attached by its first end to the second end of the fifth portion, essentially perpendicular to the fifth portion, in a second plane that is perpendicular to the first plane, its length being from 4 to 8 mm, a seventh portion attached by its first end to the second end of the sixth portion, essentially perpendicular to the sixth portion and parallel to the first portion, in the second plane, extending from the sixth portion in a direction parallel to the direction from the first end of the first portion towards the second end of the first portion, its length being from 2 to 7 mm, and an eighth portion attached by its first end to the second end of the seventh portion and by its second end to the first end of the first portion, essentially perpendicular to the seventh portion and the first portion and parallel to the sixth portion, in the second plane, its length being essentially identical to the length of the sixth portion; wherein the first portion, the second portion, the third portion, the fourth portion and the fifth portion form a stadium like form factor, wherein an inner radius in a corner defined by an attachment point between the portions is from 1 to 3 mm and an outer radius of the corners is from 2 to 6 mm; and wherein the counterpart has essentially a shape of a rectangle or ellipse, wherein a largest dimension is from 8 to 14 mm and a smallest dimension is from 6 to 12 mm, and comprises at least two openings, wherein a largest dimension of each opening is from 1 to 6 mm and a smallest dimension of each opening is from 1 to 5 mm.

13. A system according to claim 12, wherein the counterpart has the shape of a rectangle and its largest dimension is from 9 to 11 mm and its smallest dimension is from 8 to 10 mm.

14. A system according to claim 13, wherein the counterpart has the shape of a square, and its dimension is from 9 to 11 mm.

15. A system according to claim 13, wherein the shape of the openings is essentially a rectangle and its largest dimension is from 5 to 7 mm and its smallest dimension is from 1 to 3 mm.

16. A system according to claim 12, wherein the counterpart has the shape of a circle, and its diameter is from 9 to 11 mm.

17. A system according to claim 16, wherein the shape of the openings is essentially a segment of a circle, and its largest dimension is from 4 to 6 mm and its smallest dimension is from 1 to 3 mm.

18. A system according to claim 12, further comprising an artificial ligament craft.

\* \* \* \* \*